United States Patent [19]

Spivack et al.

[11] Patent Number: 4,540,732
[45] Date of Patent: Sep. 10, 1985

[54] ALKYLATED S-(HYDROXYPHENYLTHIO) ALKANOATES

[75] Inventors: John D. Spivack; Stephen D. Pastor, both of Spring Valley, N.Y.; Paul Odorisio, Palisades Park, N.J.

[73] Assignee: Ciba-Geigy Corporation, Ardsley, N.Y.

[21] Appl. No.: 547,520

[22] Filed: Oct. 31, 1983

[51] Int. Cl.³ .................... C08K 5/36; C07C 149/40
[52] U.S. Cl. ........................................ 524/289; 560/17
[58] Field of Search .......................... 524/289; 560/17

[56] References Cited

U.S. PATENT DOCUMENTS 3,285,855 11/1966 Dexter et al. .................... 524/219
3,553,163 1/1971 Spacht ............................ 524/330
3,989,664 11/1976 Kawase et al. .................... 524/289

FOREIGN PATENT DOCUMENTS 51-142097 7/1976 Japan .

OTHER PUBLICATIONS

European Patent Application No. 79855, Published May 25, 1983, (Spivack).

Primary Examiner—Veronica P. Hoke
Attorney, Agent, or Firm—Harry Falber

[57] ABSTRACT

The title compounds correspond to the formula

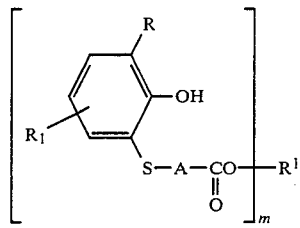

and are useful as stabilizers for organic polymers and lubricating oils to counteract the degradative effects of heat, light and air.

9 Claims, No Drawings

ALKYLATED S-(HYDROXYPHENYLTHIO) ALKANOATES

Organic polymeric materials such as plastics and resins, and lubricating and mineral oils are subject to thermal, oxidative and photo-degradation. A great variety of stabilizers are known in the art for stabilizing a diversity of substrates. Their effectiveness varies depending upon the causes of degradation and the substrate stabilized. In general, it is difficult to predict which stabilizer will be most effective and most economical for any one area of application. For example, stabilizer effectiveness in reducing volatility may depend upon preventing bond scission in the substrate molecule. Limiting embrittlement and retaining elasticity in a polymer or rubber may require prevention of excessive crosslinking and/or chain scission. Prevention of discoloration may require inhibiting reactions which yield new chromophores or color bodies in the substrate or stabilizer. Problems of process stability and incompatibility must also be considered.

It has now been determined that the S-(2-hydroxyphenylthio)alkanoates of this invention possess an unusual combination of desirable properties which makes them particularly effective and useful as stabilizers. The compounds are particularly effective in protecting polyolefins, high impact polystyrene, rubbers such as polybutadiene and styrene-butadiene rubber, and other elastomers wherein retention of elasticity and inhibition of cross-linking, crazing, discoloration, odor formation and exudation are basic requirements.

A number of p-mercaptophenol derivatives have been previously disclosed as stabilizers for organic material, in particular the S-(4-hydroxyphenylthio)alkanoates in European Patent Office Application No. 79855 published May 25, 1983, U.S. Pat. No. 3,989,664 and Japanese Kokai No. 76/142,097 published July 1976.

It is the primary object of this invention to provide a class of mercaptophenol derivatives which exhibit a broad range of improved stabilization performance characteristics, especially light-stability and color performance.

Various other objects and advantages of this invention will become evident from the following description thereof.

The compounds of this invention correspond to the formula I

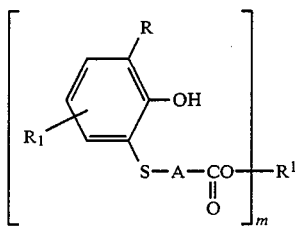

(I)

wherein

R is alkyl of 1 to 18 carbon atoms, cycloalkyl of 5 to 6 carbon atoms, phenyl, phenyl substituted by alkyl of 1 to 18 carbon atoms, aralkyl of 7 to 9 carbon atoms or said aralkyl substituted by alkyl of 1 to 18 carbon atoms;

$R_1$ is hydrogen or R,

A is $-CH(R_2)-$, $-CH(R_2)CH(R_3)-$ or $-CH_2-CH(R_2)-CH_2-$;

$R_2$ and $R_3$ are independently hydrogen or methyl;

m is 1 to 4;

when m=1, $R^1$ is alkyl of 1 to 18 carbon atoms;

when m=2; $R^1$ is alkylene of 2 to 10 carbon atoms optionally interrupted by 1 or 2 oxygen, sulfur or nitrogen atoms, alkenylene of 4 to 8 carbon atoms, alkynylene of 4 to 8 carbon atoms or cycloalkylene of 5 to 6 carbon atoms;

when m=3-4, $R^1$ is an alkane polyyl of from 3 to 6 carbon atoms.

As $C_1$-$C_{18}$ alkyl, R, $R_1$ and $R_2$ are straight-chain or branched alkyl, preferably with 1 to 8 carbon atoms, such as methyl, ethyl, propyl, isopropyl, n-butyl, sec-butyl, tert-butyl, tert-pentyl, hexyl, 2-ethyl-hexyl, n-octyl and 1,1,3,3-tetramethylbutyl.

When R and $R_1$ are aralkyl they represent benzyl, α-methylbenzyl, or α,α-dimethylbenzyl. Substituted phenyl can be for example tolyl, mesityl or xylyl.

As $C_2$-$C_{10}$ alkylene, $R^1$ can be straight-chain or branched alkylene, preferably with 2 to 6 carbon atoms, and is for example ethylene, propylene, triethylene, tetramethylene, 2,2-dimethylpropane-1,3-diyl, pentamethylene or hexamethylene. $R^1$ as alkylene interrupted by oxygen or sulfur is for example 3,6-dioxa-octamethylene or 3-thiapentamethylene. $R^1$ as alkylene interrupted by nitrogen is for example N-methyl-3-azapentamethylene.

As $C_4$-$C_8$ alkenylene, $R^1$ can be e.g. hex-3-en-1,6-ylene or preferably but-2-en-1,4-ylene.

As $C_4$-$C_8$ alkynylene, $R^1$ can be e.g. hex-3-yn-1,6-ylene or preferably but-2-yn-1,4-ylene.

$R^1$ as cycloalkylene is preferably cyclohexylene.

$R^1$ as alkane polyyl is for example a group of formula

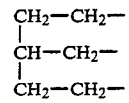

or preferably pentaerythrityl.

Preferred compounds within the compounds of formula I are those wherein R and $R_1$ are branched alkyl of 4 to 8 carbon atoms especially tert-butyl, and $R_1$ is in para position to the hydroxy group.

A is preferably $-CH_2CH_2-$ or $-CH_2CH(CH_3)-$ with $-CH_2-$ being attached to S. The subscript m is preferably 2 to 4. $R^1$ is preferably $C_1$-$C_8$ alkyl when m is 1, $C_2$-$C_6$ alkylene, 3,6-dioxaoctamethylene or 3-thiapentamethylene when m is 2; and pentaerythrityl when m is 4.

The compounds of this invention can be prepared by reacting about m moles of a thioalkanoate of the formula II

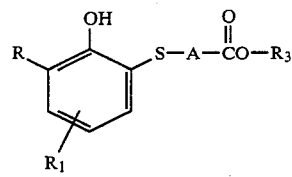

(II)

with about 1 mole of an alcohol $R^1(OH)_m$, whereby $R_3$ is lower alkyl, preferably methyl, and m, R, $R_1$, A and $R^1$ have the meanings given above, in the presence of a proton acceptor and removing the evolved lower alkyl alcohol. Typical proton acceptors include lithium salts, tertiary amines, alkali metals, alkali metal and alkaline earth metal hydroxides, carbonates, and the like. While the reaction is generally conducted in the melt, a solvent may be optionally present. The solvent is preferably aromatic, such as benzene, toluene, xylene and the like. The reaction temperature generally ranges from 75° to 200° C. Another method for preparing compounds of this invention involves reacting about m moles of a mercaptophenol of the formula III

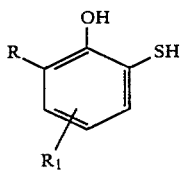

with about 1 mole of an acrylate of the formula IV

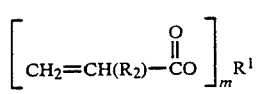

whereby m, R, $R_1$, $R_2$ and B have the meanings given above, in the presence of the above noted solvent and proton acceptor.

The starting materials utilized to prepare the compounds of the present invention are items of commerce or can be prepared by known methods. Typical alcohols $R^1(OH)_m$ include pentaerythritol, 2,2-dimethyl-1,3-propanediol, triethyleneglycol, 2,2'-thiodiethanol trimethylol propane, 1,6-hexanediol, and the like. Typical, β-unsaturated esters of the formula IV are: methyl acrylate, ethyl acrylate, n-propyl acrylate, butyl methacrylate, 2 ethylhexyl acrylate, n-dodecyl methacrylate, n-octadecyl acrylate, n-octadecyl methacrylate, pentaerythritol tetraacrylate, 1,6-hexanediol diacrylate, trimethylolpropane triacrylate, sorbitol hexaacrylate, mannitol hexaacrylate, glycerol triacrylate, ethylene glycol diacrylate, diethylene glycol diacrylate, triethylene glycol diacrylate, tetraethylene glycol dimethacrylate, and the like.

The ortho-mercaptophenol derivatives of this invention are effective in stabilizing organic materials such as plastics, polymers and resins in addition to mineral and synthetic fluids such as lubricating oils, circulating oils, etc. This effectiveness is particularly to be noted in the areas of light stability and color performance i.e. color inhibition, where these derivatives show to advantage over the aforementioned paramercaptophenol derivatives.

Substrates in which the compounds of this invention are particularly useful are polyolefins such as polyethylene and polypropylene; polystyrene, including especially impact polystyrene; ABS resin; elastomers such as e.g. butadiene rubber, EPM, EPDM, SBR and nitrile rubber.

In general polymers which can be stabilized include

1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under (1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under (5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrine homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.

8. Polymers which are derived from α,β-unsaturated acids and derivatives thereof, such as polyacrylates and polymethacrylates, polyacrylamide and polyacrylonitrile.

9. Copolymers from the monomers mentioned under (8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogen copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymer).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low inflammability.

23. Thermosetting acrylic resins, derived from substituted acrylic esters, such as epoxy-acrylates, urethane-acrylates or polyester acrylates.

24. Alkyd resins, polyester resins or acrylate resins in admixture with melamine resins, urea resins, polyisocyanates or epoxy resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatine and derivatives thereof which are chemically modified in a polymerhomologous manner, such as cellulose acetates, cellulose propionates and cellulose butyrates, or the cellulose ethers, such as methylcellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizer for polymers or as textile spinning oils, as well as aqueous emulsions of such materials.

29. Aqueous emulsions of natural or synthetic rubber, e.g. natural latex or latices of carboxylated styrene/-butadiene copolymers.

In general, the stabilizers of this invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized polymer compositions of the invention may optionally also contain various conventional additives, such as the following.

1. Antioxidants 1.1. Alkylated monophenols, for example,
2,6-di-tert.butyl-4-methylphenol
2-tert.butyl-4,6-dimethylphenol
2,6-di-tert.butyl-4-ethylphenol
2,6-di-tert.butyl-4-n-butylphenol
2,6-di-tert.butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert.butyl-4-methoxymethylphenol 1.2. Alkylated hydroquinones, for example,
2,6-di-tert.butyl-4-methoxyphenol
2,5-di-tert.butyl-hydroquinone
2,5-di-tert.amyl-hydroquinone
2,6-diphenyl-4-octadecyloxyphenol 1.3. Hydroxylated thiodiphenyl ethers, for example
2,2'-thio-bis-(6-tert.butyl-4-methylphenol)
2,2'-thio-bis-(4-octylphenol)
4,4'-thio-bis-(6-tert.butyl-3-methylphenol)
4,4'-thio-bis-(6-tert.butyl-2-methylphenol)

1.4. Alkylidene-bisphenols, for example,
2,2'-methylene-bis-(6-tert.butyl-4-methylphenol)
2,2'-methylene-bis-(6-tert.butyl-4-ethylphenol)
2,2'-methylene-bis-[4-methyl-6-(-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert.butylphenol)
2,2'-ethylidene-bis-(4,6-di-tert.butylphenol)
2,2'-ethylidene-bis-(6-tert.butyl-4-isobutylphenol)
4,4'-methylene-bis-(2,6-di-tert.butylphenol)
4,4'-methylene-bis-(6-tert.butyl-2-methylphenol)
1,1-bis-(5-tert.butyl-4-hydroxy-2-methylphenyl-butane
2,6-di-(3-tert.butyl-5-methyl-2-hydroxybenzyl)-4-methylphenol
1,1,3-tris-(5-tert.butyl-4-hydroxy-2-methylphenyl)-butane 1,1-bis-(5-tert.butyl-4-hydroxy-2-methylphenyl)-3-n-dodecylmercaptobutane
ethylenglycol-bis-[3,3-bis-(3'-tert.butyl-4'-hydroxyphenyl)-butyrate]
di-(3-tert.butyl-4-hydroxy-5-methylphenyl)-dicyclopentadien
di-[2-(3'-tert.butyl-2'-hydroxy-5'-methyl-benzyl)-6-tert.-butyl-4-methylphenyl]-terephthalate.

1.5. Benzyl compounds, for example,
1,3,5-tri-(3,5-di-tert.butyl-4-hydroxybenzyl)-2,4,6-trimethylbenzene
bis-(3,5-di-tert.butyl-4-hydroxybenzyl)-sulfide
3,5-di-tert.butyl-4-hydroxybenzyl-mercapto-acetic acid isooctyl ester
bis-(4-tert.butyl-3-hydroxy-2,6-dimethylbenzyl)dithiolterephthalate
1,3,5-tris-(3,5-di-tert.butyl-4-hydroxybenzyl)-isocyanurate
1,3,5-tris-(4-tert.butyl-3-hydroxy-2,6-dimethylbenzyl)-isocyanurate
3,5-di-tert.butyl-4-hydroxybenzyl-phosphoric acid-dioctadecyl ester
3,5-di-tert.butyl-4-hydroxybenzyl-phosphoric acid-monoethyl ester, calcium-salt 1.6. Acylaminophenols, for example,
4-hydroxy-lauric acid anilide
4-hydroxy-stearic acid anilide
2,4-bis-octylmercapto-6-(3,5-tert.butyl-4-hydroxyanilino)-s-triazine
octyl-N-(3,5-di-tert.butyl-4-hydroxyphenyl)-carbamate 1.7. Esters of β-(3,5-di-tert.butyl-4-hydroxyphenyl)-propionic acid with monohydric or polyhydric alcohols, for example,

| methanol | diethyleneglycol |
| octadecanol | triethyleneglycol |
| 1,6-hexanediol | pentaerythritol |
| neopentylglycol | tris-hydroxyethyl isocyanurate |
| thiodiethyleneglycol | di-hydroxyethyl oxalic acid diamide |

1.8. Ester of β-(5-tert.butyl-4-hydroxy-3-methylphenyl)-propionic acid with monohydric or polyhydric alcohols, for example,

| methanol | diethyleneglycol |
| octadecanol | triethyleneglycol |
| 1,6-hexanediol | pentaerythritol |
| neopentylglycol | tris-hydroxyethyl isocyanurate |
| thiodiethyleneglycol | di-hydroxyethyl oxalic diamide |

1.9. Amides of β-(3,5-di-tert.butyl-4-hydroxyphenyl)-propionic acid for example,
N,N'-bis-(3,5-di-tert.butyl-4-hydroxyphenylpropionyl)-hexamethylenediamine
N,N'-bis-(3,5-di-tert.butyl-4-hydroxyphenylpropionyl)-trimethylenediamine
N,N'-bis-(3,5-di-tert.butyl-4-hydroxyphenylpropionyl)-hydrazine 2. UV absorbers and light stabilisers 2.1. 2-(2'-Hydroxyphenyl)-benztriazoles, for example, the 5'-methyl-, 3',5'-di-tert.butyl-, 5'-tert.butyl-, 5'-(1,1,3,3-tetramethylbutyl)-, 5-chloro-3',5'-di-tert.-butyl-, 5-chloro-3'-tert.butyl-5'-methyl-, 3'-sec.butyl-5'-tert.butyl-, 4'-octyloxy, 3',5'-di-tert.amyl-, 3',5'-bis-(α,α-dimethylbenzyl)-derivative.

2.2. 2-Hydroxy-benzophenones, for example, the 4-hydroxy-, 4-methoxy-, 4-octyloxy, 4-decyloxy-, 4-dodecyloxy-, 4-benzyloxy, 4,2',4'-trihydroxy- and 2'-hydroxy-4,4'-dimethoxy derivative.

2.3. Ester of optionally substituted benzoic acids for example, phenyl salicylate, 4-tert.butyl-phenylsalicylate, octylphenyl salicylate, dibenzoylresorcinol, bis-(4-tert.-butylbenzoyl)-resorcinol, benzoylresorcinol, 3,5-di-tert.-butyl-4-hydroxybenzoic acid 2,4-di-tert.butylphenyl ester and 3,5-di-tert.-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5 Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-di-ethanolamine, nickel dibutyldithiocarbamate, nickel salts of 4-hydroxy-3,5-di-tert.butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazol, optionally with additional ligands.

2.6. Sterically hindered amines, for example bis-(2,2,6,6-tetramethylpiperidyl)-sebacate bis-(1,2,2,6,6-pentamethylpiperidyl)-sebacate n-butyl-3,5-di-tert.butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert.octylamino-2,6-dichloro-1,3,5-s-triazine, tris-(2,2,6,6-tetramethylpiperidyl)-nitrilotriacetate, tetrakis-(2,2,6,6-tetramethyl-4-piperidyl)-1,2,3,4-butane-tetracarbonic acid, 1,1'(1,2-ethanediyl)-bis-(3,3,5,5-tetramethylpiperazinone).

2.7. Oxalic acid diamides, for example 4,4'-di-octyloxyoxanilide, 2,2'-di-octyloxy-5,5'-di-tert.butyl-oxanilide, 2,2'-di-dodecyloxy-5,5'-di-tert.butyl-oxanilide, 2-ethoxy-2'-ethyl-oxanilide, N,N'-bis(3-dimethylaminopropyl)-oxalamide, 2-ethoxy-5-tert.butyl-2'-ethyloxanilide and its mixture with 2-ethoxy-2'-ethyl-5,4'-di-tert.butyloxanilide and mixtures of ortho- and para-methoxy-as well as of o-and p-ethoxy-disubstituted oxanilides.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert.butyl-4-hydroxyphenylpropionyl)-hydrazine, 3-salicyloylamino-1,2,4-triazole bis-benzylidene-oxalic acid dihydrazide.

4. Phosphites and phosphonites, for example, triphenyl phosphite, diphenylalkyl phosphites, phenyldialkyl phosphites, tri-(nonylphenyl)phosphite, trilauryl phosphite, trioctadecyl phosphite, di-stearyl-pentaerythrityl diphosphite, tris-(2,4-di-tert.butylphenyl)-phosphite, di-isodecylpentaerythrityl diphosphite, di-(2,4-di-tert.butylphenyl)pentaerythrityl diphosphite, tristearyl-sorbityl triphosphite, tetrakis-(2,4-di-tert-.butylphenyl)-4,4'-diphenylendiphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc-dibutyl-dithiocarbamate, dioctadecyldisulfide, pentaerythrityl-tetrakis-(β-dodecylmercapto)-propionate.

6. Polyamide stabilizers, for example copper salts in combination with iodides and/or phosphorus compounds and salts of divalent manganese.

7. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

8. Nucleating agents, for eample, 4-tert.butyl-benzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxides, carbon black, graphite.

10. Other additives, for example, plasticizers, lubricants, emulsifiers, pigments, optical brighteners, flameproofing agents, anti-static agents, blowing agents and thiosynergists such as dilaurylthiodipropionate or distearylthiodipropionate.

The following examples illustrate the embodiments of this invention. In these examples, all parts given are by weight unless otherwise specified.

EXAMPLE 1

3-(3,5-Di-tert-butyl-2-hydroxyphenylthio)propanoic acid methyl ester

In a 50 ml flask under nitrogen, a mixture of 5.00 grams of 2,4-di-tert-butyl-6-mercaptophenol, 1.80 grams of methyl acrylate and 20 mls toluene was treated with 0.50 mls of triethylamine. After stirring for three hours at ambient temperature, the solvent was removed in vacuo. The residue was purified by chromatography on silica gel using toluene/heptane eluent to give 3.90 g (57% yield) of a colorless oil.

Anal. Calcd for $C_{18}H_{28}O_3S$: S, 9.9. Found: S, 10.1.

EXAMPLE 2

3-(3,5-Di-tert-butyl-2-hydroxyphenylthio)propanoic acid (2-ethylhexyl)ester

The procedure of Example 1 was repeated using 20.0 grams of 2,4-di-tert-butyl-6-mercaptophenol, 15.5 grams of 2-ethylhexyl acrylate, 0.25 ml of triethylamine and 150 mls of toluene. The residue was purified by chromatography on silica gel using toluene/heptane eluent to give 12.4 g (35% yield) of a colorless oil.

Anal. Calcd for $C_{25}H_{42}O_3S$: C, 71.0; H, 10.0; S, 7.6. Found: C, 71.4, H, 10.4; S, 7.4.

EXAMPLE 3

Bis[3-(3,5-di-tert-butyl-2-hydroxyphenylthio)-2-methyl propanoic acid]triethyleneglycol diester In a 200 ml flask under nitrogen, a solution of 23.8 grams of 2,4-di-tert-butyl-6-mercaptophenol in 50 mls toluene was treated with 0.04 grams of lithium hydride. After stirring the resultant mixture for one half hour, 14.3 grams of triethylene glycol dimethacrylate was added. The mixture was then heated at 80° C. until disappearance of reactants as determined by thin layer chromatography analysis (approximately two hours). The reaction was then treated with 10 ml of 1N aqueous hydrochloric acid and the layers separated. The organic layer was dried (Na$_2$SO$_4$) and concentrated in vacuo. The residue was purified by chromatography on silica gel using ethyl acetate/methylene chloride eluent to give 10.0 g (26% yield) of a colorless viscous liquid.

Anal. Calcd for $C_{42}H_{66}O_8S_2$: C, 66.1; H, 8.7; C, 8.4. Found: C, 66.0; H, 8.3; S, 8.6.

EXAMPLE 4

Tetrakis-[3-(3,5-di-tert-butyl-2-hydroxyphenylthio)-propanoic acid]pentaerythritol tetraester In a 100 ml flask equipped with a Dean Stark trap, a mixture of 30.0 grams of the compound of Example 1, 3.15 grams of pentaerythritol and 0.02 grams of lithium hydride was heated at 140°–165° C. at 50 mm Hg for 11 hours. The reaction residue was purified by chromatography on silica gel using ethyl acetate/heptane eluent to give 16.0 g (53% yield) of a colorless solid, m.p. 124°–127° C.

Anal. Calcd for $C_{73}H_{108}O_{12}S_4$; C, 67.1; H, 8.3; S, 9.8. Found: C, 67.3; H, 8.4; S, 9.5.

EXAMPLE 5

Bis[3-(3,5-di-tert-butyl-2-hydroxyphenylthio)propanoic acid]2,2'-thiodiethyl diester The procedure of Example 4 was repeated using 30.0 grams of the compound of Example 1, 5.64 grams of 2,2'-thiodiethanol and 0.02 grams of lithium hydride. The reaction residue was purified by chromatography on silica gel using toluene/ethyl acetate eluent to give 22.0 g (67% yield) of a colorless solid, m.p. 64°–66° C.

Anal. Calcd for $C_{38}H_{58}O_6S_3$: S, 13.6. Found: S, 13.2

EXAMPLE 6

Stabilization of polypropylene (Light stability)

Unstabilized polypropylene powder (Hercules Profax 6501) is thoroughly blended with 0.2% by weight, of additive. The blended materials are then milled on a two roll mill at 182° C. for five minutes, after which time the stabilized polypropylene is sheeted from the mill and allowed to cool. The milled polypropylene is then cut into pieces and compression molded on a hydraulic press at 220° C. and 175 psi ($1.2 \times 10^6$ Pa) into 5 mil (0.127 mm) films. The sample is exposed in a fluorescent sunlight/black light chamber until failure. Failure is taken as the hours required to reach 0.5 carbonyl absorbance by infrared spectroscopy on the exposed films.

| Additive | Hours to Failure |
|---|---|
| None | 250 |
| Example 2 | 420 |
| Example 3 | 370 |
| Example 4 | 370 |
| Example 5 | 400 |

EXAMPLE 7

Stabilization of polypropylene (Oxidation stability)

The oxidation stability of the milled polypropylene samples from Example 6 containing 0.2% by weight of additive as well as that of a synergized formulation containing 0.1% by weight of additive in the presence of 0.3% by weight distearyl thiodipropionate (DSTDP) on plaques of 25 mil (0.635 mm) thickness is determined by exposing said plaques to air in a forced draft oven at 150° C. The plaques are considered to have failed on showing the first signs of decomposition (e.g., cracking or brown edges).

| Additive | Hours to Failure |
| --- | --- |
| Base Resin | <20 |
| Base Resin with 0.3% DSTDP | <20 |
| Example 3 | 70 |
| Example 4 | 100 |
| Example 4 with DSTDP | 140 |
| Example 5 | 110 |

EXAMPLE 8

Stabilization of impact polystyrene

In a laboratory procedure utilized herein, a solution of eight (8) weight percent polybutadiene rubber (Firestone DIENE 55) dissolved in styrene monomer is prepared on a roller mill. 0.1% by weight of stabilizer is also introduced at this point. 500 ppm of zinc stearate are added to aid in removing the sample from the bottle after the polymerization. The bottle is screwed into the polymerization apparatus which is equipped with a double helical ribbon stirrer. Since most commercial IPS bulk polymerization are thermally initiated processes, no initiator is used in the laboratory process. A nitrogen atmosphere is established and the reactor is then heated to 121° C. within ½ hour. Heating continues at 121° C. with efficient stirring until there is a 30 to 35% monomer conversion (2.5 hours). The stirring rate is controlled to yield a two to four μm rubber particle size. The bottles are removed from the polymerization apparatus, blanketed with nitrogen, capped, and then placed in a fluidized bed sand bath to complete the polymerization. The bottles are heated in the bath in the following fashion: one hour at 100° C. to equilibrate the temperature, one hour to reach 140° C. and then an additional eight hours with the temperature increasing at the rate of 10° C. per hour to a maximum of 220° C. After the resin has cooled, the bottle is broken and the glass removed. The average weight of the polymer block is slightly over 600 grams. The block is then placed into a vacuum oven at 200° C. and a vacuum of 1 mm applied as the polymer is heated for 45 minutes in order to remove all volatiles. The block is removed from the oven, immediately placed in a heated (205° C.) hydraulic press and then pressed into a thick slab between two sheets of aluminum foil (three minutes heating, five minutes in a cold press). The slab is split with a hand saw and the pieces granulated.

All batches are extruded at 205° C. and then pelletized. The pellets are compression molded at 205° C. into 125 mil (3.175 mm) bars. The bars ae then aged at 150° C. on glass plates placed on rotating shelves in a forced air oven. The specimen yellowness index is determined on the bars at various intervals according to ASTM D-1925-63T.

| Additive | Oven Aged Samples at 150° C. | | | |
| --- | --- | --- | --- | --- |
| | Hours at 150° C. | | | |
| | 0 | ½ | 1 | 1½ | 2 |
| | Yellowness Index | | | |
| None | 7 | 18 | 30 | 38 | 43 |
| Example 4 | −2 | 0 | 4 | 4 | 15 |

Examples 6, 7 and 8 thus indicate the significantly better performance of the instant compounds as compared to the base resin.

Summarizing, it is seen that this invention provides a group of compounds which exhibit effective stabilizing activity in a variety of organic materials. Variations may be made in proportions, procedures and materials without departing from the scope of the invention as defined by the following claims.

What is claimed is:

1. The compound of the formula

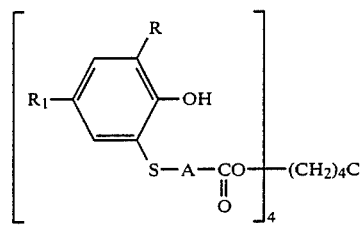

wherein
R and $R_1$ are alkyl of 1 to 18 carbon atoms, cycloalkyl of 5 to 6 carbon atoms, phenyl, phenyl substituted by alkyl of 1 to 18 carbon atoms, aralkyl of 7 to 9 carbon atoms or said aralkyl substituted by alkyl of 1 to 18 carbon atoms;
A is —CH($R_2$)—, —CH($R_2$)CH($R_3$)— or —CH$_2$—CH($R_2$)—CH$_2$—; and
$R_2$ and $R_3$ are independently hydrogen or methyl.

2. The compound of claim 1, wherein R and $R_1$ are branched alkyl of 4 to 8 carbon atoms.

3. The compound of claim 2, wherein R and $R_1$ are tert-butyl.

4. The compound of claim 1, wherein A is —CH$_2$CH$_2$— or —CH$_2$CH(CH$_3$)— with —CH$_2$— being attached to S.

5. A compound according to claim 1 tetrakis-[3-(3,5-di-tert-butyl-2-hydroxyphenylthio)propanoic acid]pentaerythritol tetraester.

6. A composition of matter comprising an organic material subject to oxidative, thermal and actinic degradation stabilized with an effective stabilizing amount of a compound of claim 1.

7. The composition of claim 6, wherein the organic material is a synthetic polymer.

8. The composition of claim 7, wherein said polymer is selected from the group consisting of polyolefins, impact polystyrene, acrylonitrile-butadiene styrene copolymer resin, butadiene rubber, ethylene-propylene copolymer ethylene-propylene- diene copolymer styrene-butadiene copolymer and nitrile rubber.

9. A method for stabilizing an organic material against oxidative, thermal and actinic degradation which comprises incorporating into said organic material an effective stabilizing amount of a compound of claim 1.

* * * * *